US011642185B2

(12) United States Patent
Cappelleri et al.

(10) Patent No.: US 11,642,185 B2
(45) Date of Patent: May 9, 2023

(54) SYSTEMS AND METHODS FOR PERFORMING A SURGICAL PROCEDURE

(71) Applicant: Purdue Research Foundation, West Lafayette, IN (US)

(72) Inventors: David John Cappelleri, West Lafayette, IN (US); Yang Ding, Shanghai (CN); Benjamin Varughese Johnson, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 592 days.

(21) Appl. No.: 16/714,993

(22) Filed: Dec. 16, 2019

(65) Prior Publication Data
US 2021/0177528 A1    Jun. 17, 2021

(51) Int. Cl.
*A61B 34/30* (2016.01)
*A61B 17/00* (2006.01)

(52) U.S. Cl.
CPC ........ *A61B 34/30* (2016.02); *A61B 17/00234* (2013.01); *A61B 2017/00261* (2013.01); *A61B 2017/00398* (2013.01); *A61B 2034/301* (2016.02); *A61B 2034/303* (2016.02)

(58) Field of Classification Search
CPC . A61B 19/201; A61B 19/203; A61B 19/5244; A61B 34/30; A61B 17/00; A61B 17/00234; A61B 2017/00398; A61B 2017/00261
See application file for complete search history.

(56) References Cited

U.S. PATENT DOCUMENTS

| 2015/0250498 A1* | 9/2015 | Kikuchi | A61B 17/3421 604/164.01 |
| 2015/0366572 A1* | 12/2015 | Sholev | A61B 17/29 606/1 |
| 2017/0027606 A1* | 2/2017 | Cappelleri | A61B 1/018 |

\* cited by examiner

*Primary Examiner* — Vi X Nguyen
(74) *Attorney, Agent, or Firm* — Hartman Global IP Law; Gary M. Hartman; Domenica N. S. Hartman

(57) ABSTRACT

Systems and methods for performing surgical procedures. Such a system includes a cannula having proximal and distal portions. At least one carriage unit is slidably mounted within the proximal portion of the cannula for translation in axial directions of the cannula, and a tool has a shaft that is coupled to the carriage unit and protrudes through a port at the distal portion of the cannula. The tool has a working element mounted on a portion of the shaft that protrudes from the cannula to perform tasks within the cavity. A translation mechanism is provided for translating the carriage unit and its tool in the axial directions of the cannula, and a rotation mechanism is provided for rotating the tool about an axis of its shaft and relative to the first carriage unit. Rotation and translation mechanisms of each carriage unit are preferably individually and independently controlled.

20 Claims, 19 Drawing Sheets

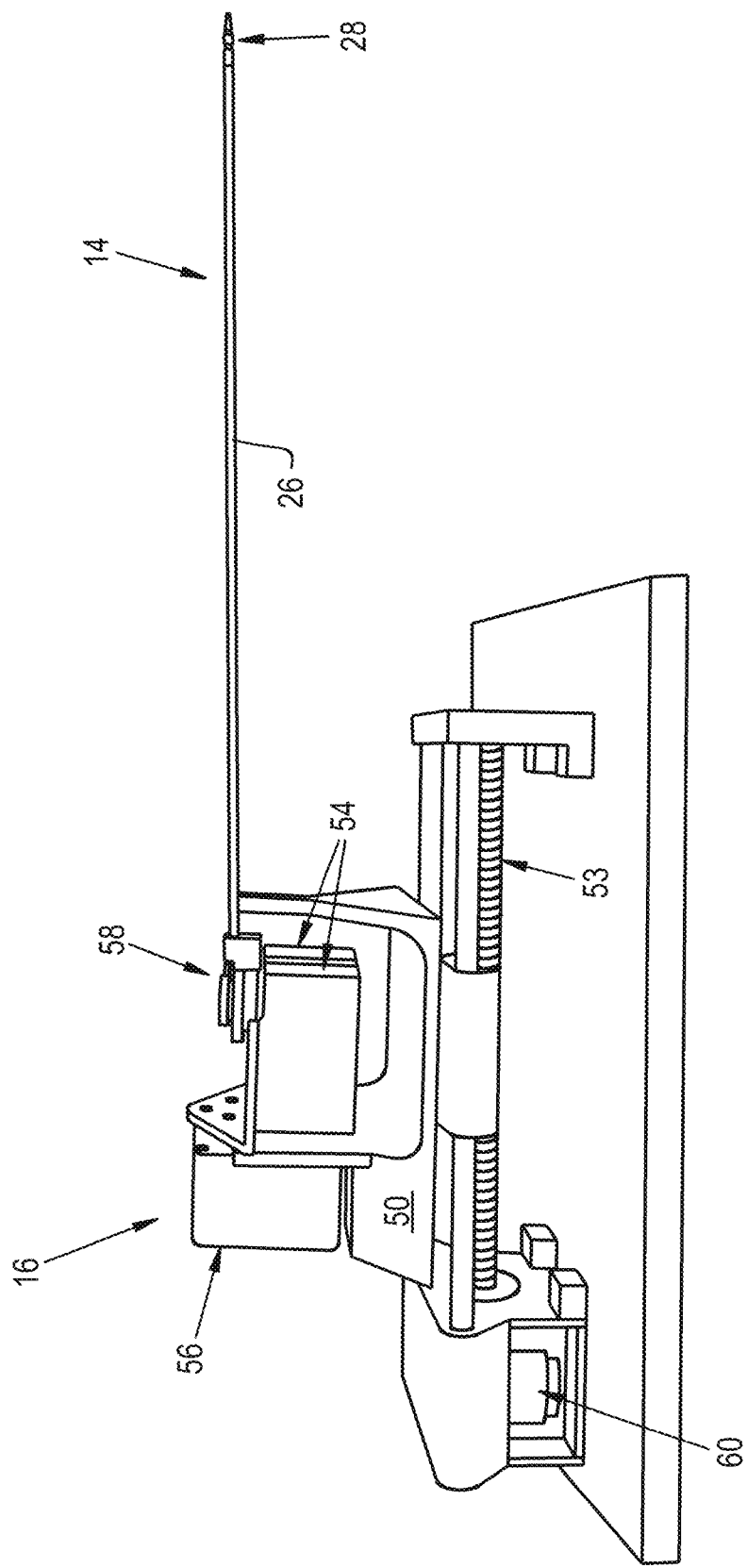

SYSTEMS AND METHODS FOR PERFORMING A SURGICAL PROCEDURE

CROSS REFERENCE TO RELATED APPLICATIONS

This application is related to co-pending U.S. patent application Ser. No. 15/871,622 filed Jan. 15, 2018, which is a continuation-in-part patent application of co-pending U.S. patent application Ser. No. 15/222,998 filed Jul. 29, 2016, both of which claim the benefit of U.S. Provisional Application No. 62/199,733, filed Jul. 31, 2015. The contents of these prior applications are incorporated herein by reference.

BACKGROUND OF THE INVENTION

The present invention generally relates to tools for working in relatively small working spaces with limited access. The invention particularly relates to instruments for use in minimally invasive surgical procedures.

Pain within an individual's lower back, specifically the lumbar region of the spine, is typically induced by disc herniations or over-compression of the vertebrae. To treat this discomfort, surgeons may perform a microdiscectomy, a minimally invasive (as opposed to open surgery) technique for removing a portion of the herniated disc material that is pressing on the nerve root. While these surgical procedures typically have high success rates and improve patient outcomes relative to more invasive procedures, the tools currently available for performing minimally invasive procedures have limitations.

Surgical instruments commonly available for removing herniated disc material include rigid probes with tips that manipulate and remove tissue. Nonlimiting examples of such instruments include a set of tools available from Richard Wolf Medical Instruments Corporation under the name VERTEBRIS™, a disposable set of tools available from Vertos Medical Inc. under the name Mild®, and a single-use tool available from Stryker Corporation under the name Dekompressor®. Due to the limited working space within the lumbar region of the spine, the limited dexterity of available tools capable of manipulating and removing tissue, and limited vision sometimes encountered during a minimally invasive procedure, a surgeon may become uncomfortable over time and may be forced to operate blindly for portions of the procedure. In addition, movement of a tool, commonly formed of rigid materials to achieve orientations often required during a minimally invasive procedure, can cause inadvertent damage to muscles, soft tissue, and nerve roots.

While most available surgical instruments used in minimally invasive procedures are rigid, some more recent instruments have been disclosed that are based on a flexible backbone structure to provide improved flexibility. However, such tools typically have a relatively large radius of curvature and hence can be used only in relatively large body cavities and similarly sized working spaces. Although surgical tools have been disclosed having diameters less than four millimeters, they are often expensive to manufacture and require complicated assembly.

Robotic surgical systems are now emerging which are intended to overcome challenges associated with surgical procedures. However, these systems are generally limited in their practical applications due to their size, capabilities, and cost. Additionally, these systems may require extensive sterilization and draping to reduce the risk of infection.

In view of the above, there is an ongoing desire for devices that are capable of use in surgical procedures, for example, minimally invasive procedures such as microdiscectomy, with improved dexterity and vision relative to currently available surgical instruments.

BRIEF DESCRIPTION OF THE INVENTION

The present invention provides systems and methods for performing surgical procedures with improved dexterity and vision relative to systems and methods performed with currently available surgical instruments used in minimally invasive procedures.

According to one aspect of the invention, a system for performing a surgical procedure within a cavity of a living body includes a cannula having a proximal portion, a distal portion sized and configured to be inserted into the cavity, and multiple ports located at a distal end of the distal portion. At least a first carriage unit is slidably mounted within the proximal portion of the cannula for translation in axial directions of the cannula, and at least a first tool has a shaft that is coupled to the first carriage unit and protrudes through at least a first port of the multiple ports of the distal portion of the cannula. The first tool has a working element mounted on a portion of the shaft that protrudes from the cannula, and the working element is configured to perform tasks within the cavity. A translation mechanism is provided for translating the first carriage unit and the first tool thereof in the axial directions of the cannula, and a rotation mechanism is provided for rotating the first tool about an axis of the shaft of the first tool and relative to the first carriage unit.

Technical effects of a system as described above preferably include the ability to perform tasks of a surgical procedure in a cavity of a living body with improved precision and dexterity relative to currently available surgical instruments used in minimally invasive procedures.

Other aspects and advantages of this invention will be appreciated from the following detailed description.

BRIEF DESCRIPTION OF THE DRAWINGS

FIG. 8 shows a surgical instrument coupled to an actuator unit in accordance with a nonlimiting embodiment of this invention.

DETAILED DESCRIPTION OF THE INVENTION

Figure 1:
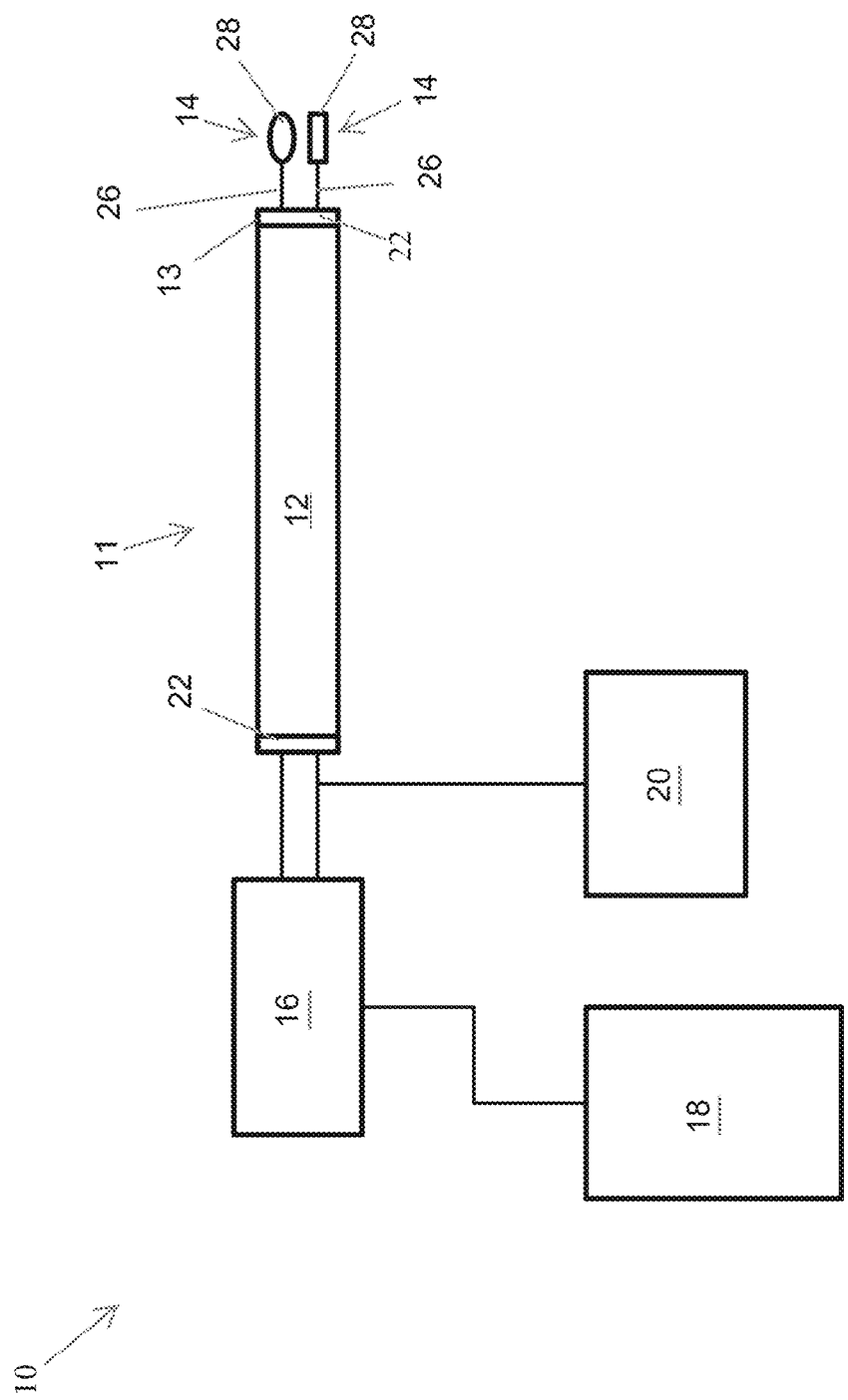
FIG. 1 schematically represents a system comprising a surgical instrument equipped with multiple tools for performing tasks in an enclosed space in accordance with a nonlimiting embodiment of this invention.

FIG. 1 schematically represents a system 10 equipped with a surgical instrument 11 configured to perform tasks in a confined working space or cavity. Although the system 10 will be described below as being used to perform tasks associated with or required by a minimally invasive surgical procedure within a cavity of a living body, such as but not limited to a microdiscectomy performed in a human being, it is within the scope of the invention that the system 10 could be configured for use in any type of confined working space or cavity. For example, the system 10 may be configured for use in a surgical procedure or other invasive procedures performed on animals, or may be used in a non-medical field to repair or otherwise access and manipulate objects in difficult to access locations. It is within the scope of the invention that the confined working space or cavity in which the system 10 is configured to perform tasks may be relatively small, for example, having a volume of about ten cubic centimeters or less, and as small as about three cubic centimeters or less. As a matter of convenience, the terms "distal" and "proximal" are used herein in reference to the locations of various features of the system 10 with respect to an operator of the system 10 while using the system 10 to perform a surgical procedure within a cavity of a living body.

The system 10 is represented in FIG. 1 as including the surgical instrument 11 functionally coupled to an actuator unit 16. The instrument 11 is represented as comprising a cannula 12 having a distal end 13 sized and configured for insertion through an incision in a patient during a minimally invasive surgical procedure. Although the body of the cannula 12 could have any shape, it is represented in the drawings as having an elongated tubular body. The cannula 12 is configured to allow one or more surgical tools 14 to be routed therethrough, such that a working element 28 of each tool 14 protrudes from the distal end 13 of the cannula 12. The working elements 28 are configured to manipulate and/or remove tissue during the surgical procedure. A control system 18 is provided that enables a surgeon to operate and control the instrument 11, for example, a computer or other processing device with manual controls such a joystick for performing the surgical procedure or on which a computer program is running with software instructions for implementing the surgical procedure. FIG. 1 further represents a monitor 20 for displaying video images captured by a camera within an incision. Such a camera may be incorporated as the working element 28 on one of the tools 14.

Figure 2:
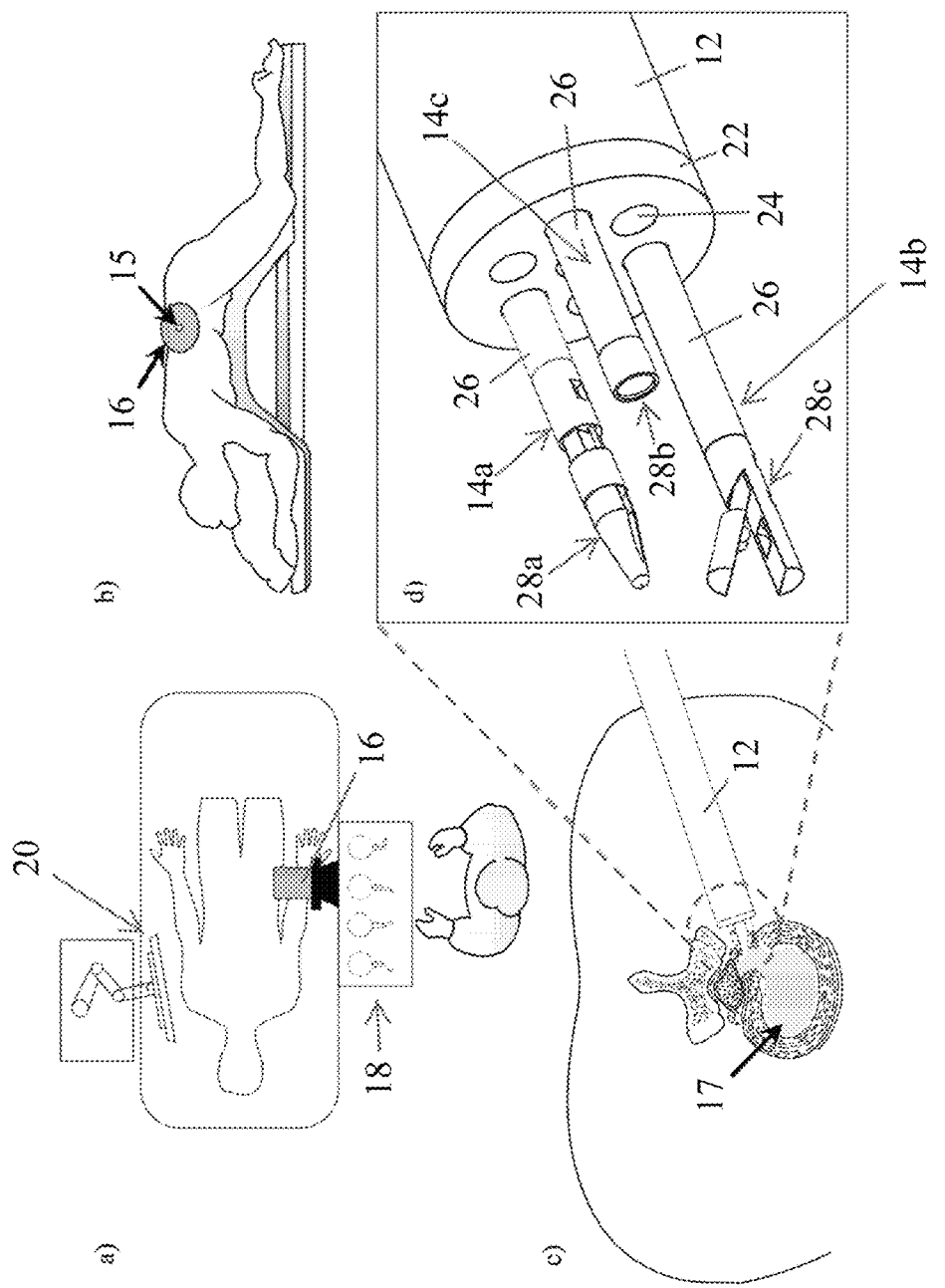
FIG. 2 includes images a, b, c, and d, which schematically represent use of the system of FIG. 1 during a microdiscectomy in accordance with a nonlimiting embodiment of this invention.

Images (a) through (c) of FIG. 2 schematically represent a nonlimiting embodiment of the system 10 as configured for performing a microdiscectomy, during which an incision is made to manipulate and/or remove tissue. Image (a) represents a surgeon positioned adjacent an operating table on which a patient lies. The control system 18 enables the surgeon to operate the instrument 11 using manual controls that provide control of the cannula 12, the tools 14, and the working elements 28. The system 10 may have means for selectively locking the position of an individual working element 28, for example, so that the surgeon can efficiently operate the working element 28 of a different tool 14. The monitor 20 is located on an opposite side of the operating table to provide the surgeon with a clear view of video images captured within the incision. During the procedure, the distal end 13 of the cannula 12 may be inserted into the patient through an incision 15 to interact with herniated disk material 17.

Figure 3:
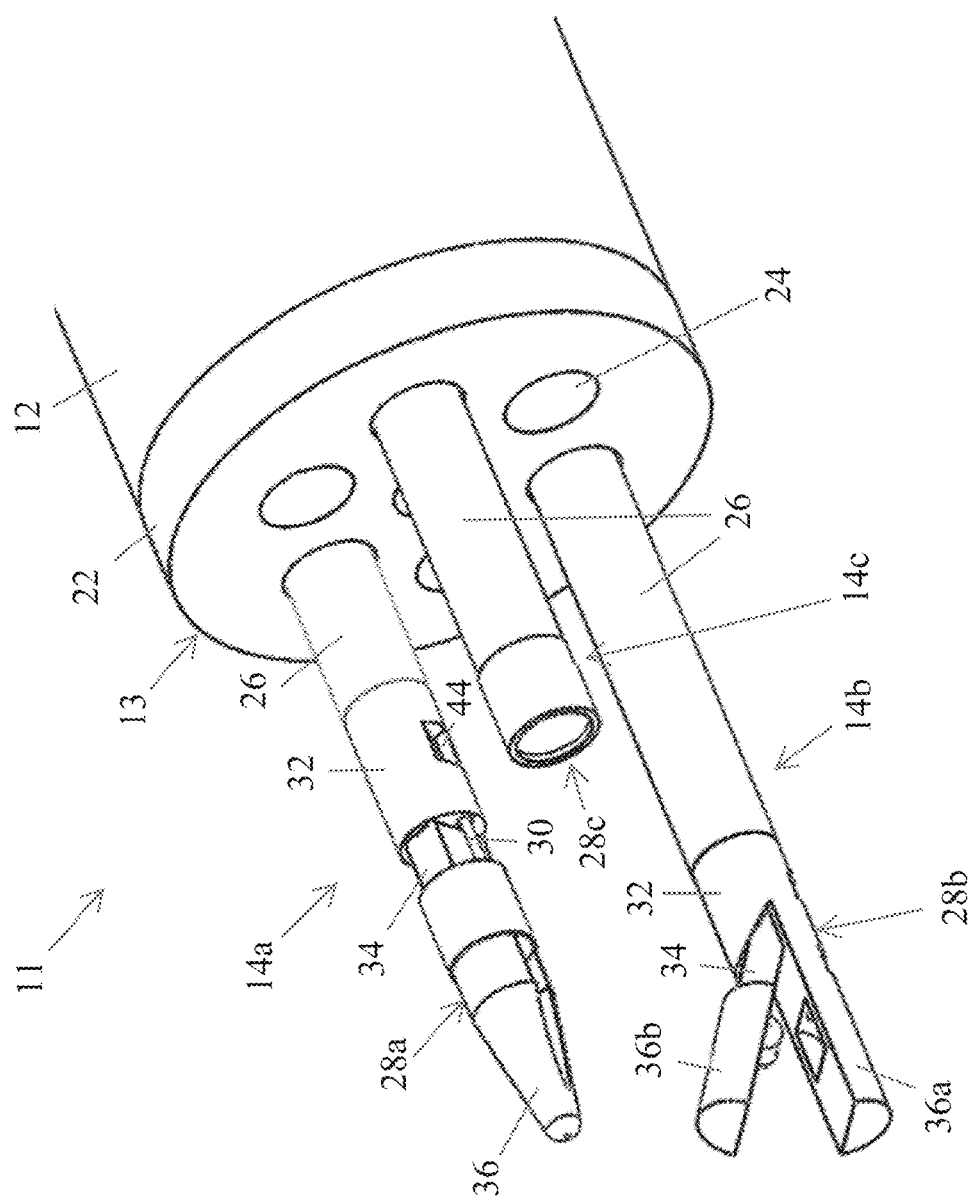
FIG. 3 is an enlarged view of a distal end of the surgical instrument of FIG. 2.

Image (d) of FIG. 2 and FIG. 3 schematically represent the distal end 13 of the cannula 12 as including an adapter 22 comprising several ports 24 from which the tools 14 may protrude. As represented in FIG. 1, the oppositely disposed proximal end of the cannula 12 also preferably includes a similar adapter 22. Each adapter 22 has multiple ports 24 formed therein that provide spacing between and support for the various tools 14, which preferably are capable of being retracted within the cannula 12. Although represented as through-holes having circular cross-sections, the ports 24 may each individually be any shape and/or size to allow passage through and support of a corresponding tool 14. As a nonlimiting example, one or more of the ports 24 may be through-holes having a circular cross-section having a diameter of 0.125 inch (about 3 mm) or more.

FIG. 8 represents an individual tool 14 as including an elongated shaft 26 having a working element 28 on a distal end thereof. The shaft 26 may be of any diameter (or width) and length, comparable devices being in the nonlimiting ranges of 0.125 inch (about 3 mm) diameter or less and between about 150 and 200 micrometers long. Preferably, the shaft 26 is capable of individually rotating within the cannula 12, and the working elements 28 are capable of articulation relative to the shaft 26. Such functionality provides the ability to change the orientation of the working elements 28 during a surgical procedure without moving the cannula 12, thus reducing damage to tissues surrounding the cannula 12.

As a nonlimiting example, FIG. 3 represents three tools 14a, 14b, and 14c protruding from the distal end 13 of the cannula 12. The tools 14a, 14b, and 14c include working elements 28a, 28b, and 28c on their distal end which are configured to function as a nerve retractor, a grasper, and a camera, respectively. The working element 28a of the tool 14a includes a tip 36 coupled to a base 32 by a flexible joint 34. The base 32 secures the working element 28a to the shaft 26 and may comprise any fastener, threads, or other means for securing the working element 28a to the shaft 26 or may comprise a structure that in conjunction with a fastener is capable of securing the working element 28a to the shaft 26. For example, FIG. 5 represents the working element 28 as comprising a structure 72 for mating with and press-fitting within the shaft 26.

Figure 4:
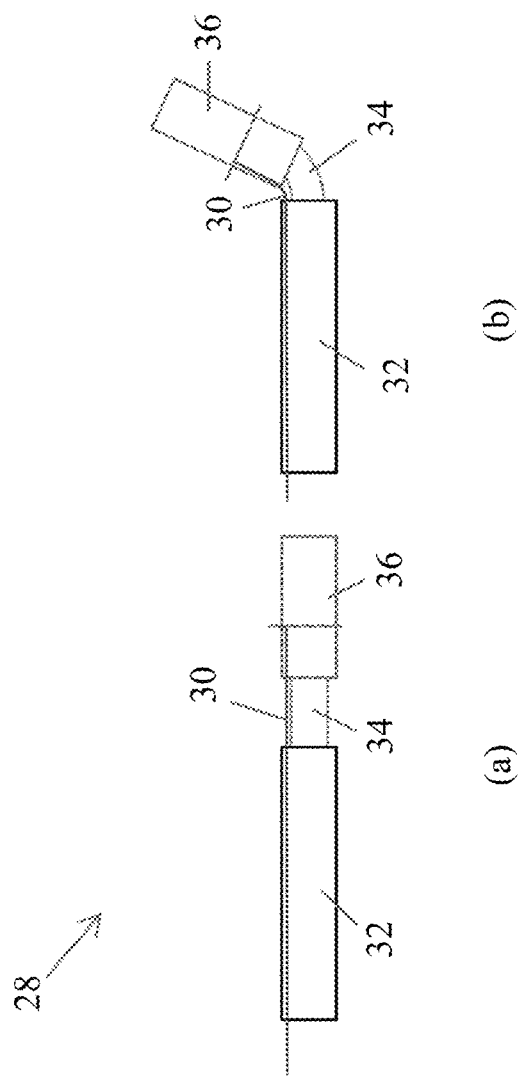
FIG. 4 includes images a and b, which schematically represent articulation of a working element of a tool in accordance with a nonlimiting embodiment of this invention.

FIG. 4 represents a working element 28 of any tool 14, and the manner in which the flexible joint 34 thereof allows the tip 36 to be articulated relative to the base 32. To facilitate such articulation, at least two guide wires 30 may be coupled to the tip 36 and threaded through the working element 28, into the shaft 26, and through the shaft 26 to the proximal end of the cannula 12, where the guide wires 30 may be functionally coupled to, for example, the actuator unit 16 (FIGS. 1, 2, and 8). FIG. 8 represents a nonlimiting embodiment of the actuator unit 16 as connected to the shaft 26 of the tool 14. As also represented in FIG. 8, the actuator unit 16 may comprise servo motors 54 and pulleys 58 for selectively providing or releasing tension on the guide wires 30 to manipulate the working elements 28, an additional servo motor 56 for rotating the shaft 26, and a platform 50, lead screw 53, and stepper motor 60 for retracting or extending the working element 28 mounted on the shaft 26. It should be understood that these components may be substituted with other means capable of selectively providing or releasing tension on the guide wires 30 to retract or extend each tool 14, articulate its working element 28, rotate the working element 28, or otherwise manipulate the tip 36 of the working element 28. Preferably, each working element 28 has a range of motion of at least 80 degrees of rotation (yaw).

The tip 36 of the working element 28 may be any device capable of assisting in the performance of the surgical procedure. For example, in addition to or as alternatives of the retractor 28a, grasper 28b, and camera 28c described for the working elements 28 of FIG. 3, the tip 36 of the working element 28 may be a surgical manipulator (such as but not limited to a rongeur, an elevator, a hook, a curette, a dissector, a scalpel, etc.), a suction tip of an irrigation system, a drill, or any other device.

Figure 5:
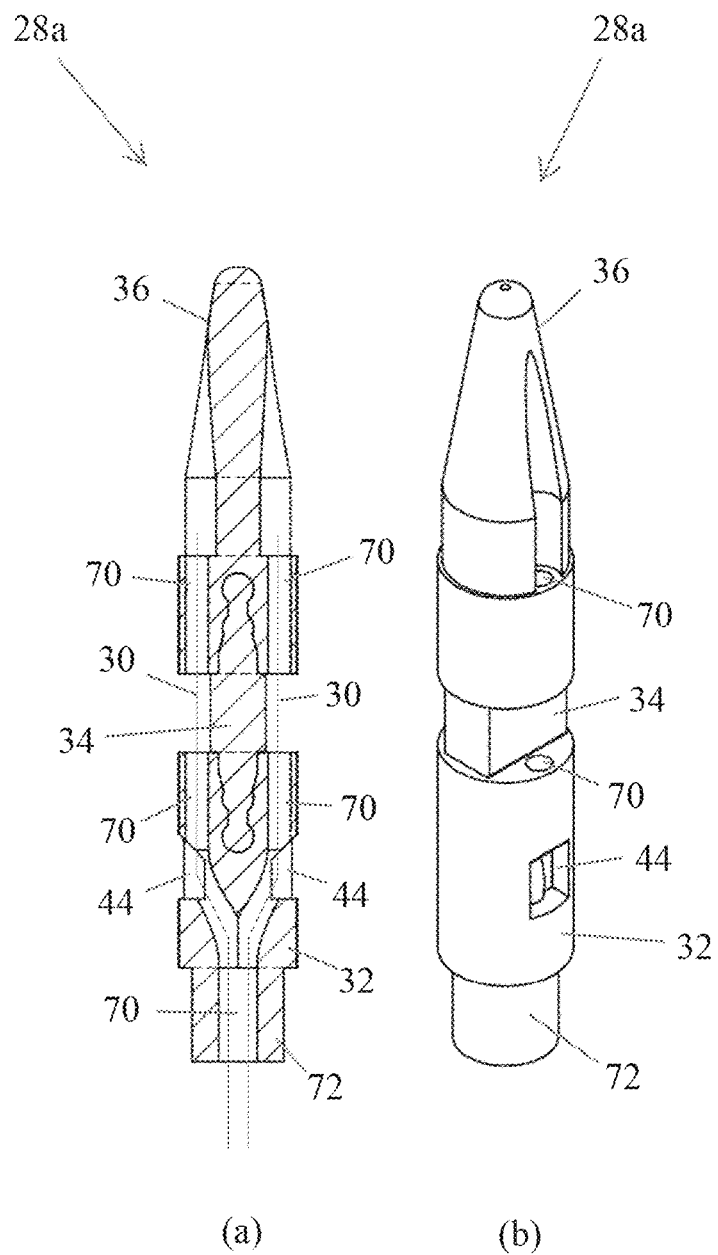
FIG. 5 includes images a and b, which are cross-sectional and perspective views, respectively, that schematically represent a nonlimiting working element configured as a nerve retractor in accordance with a nonlimiting embodiment of this invention.
Figure 6:
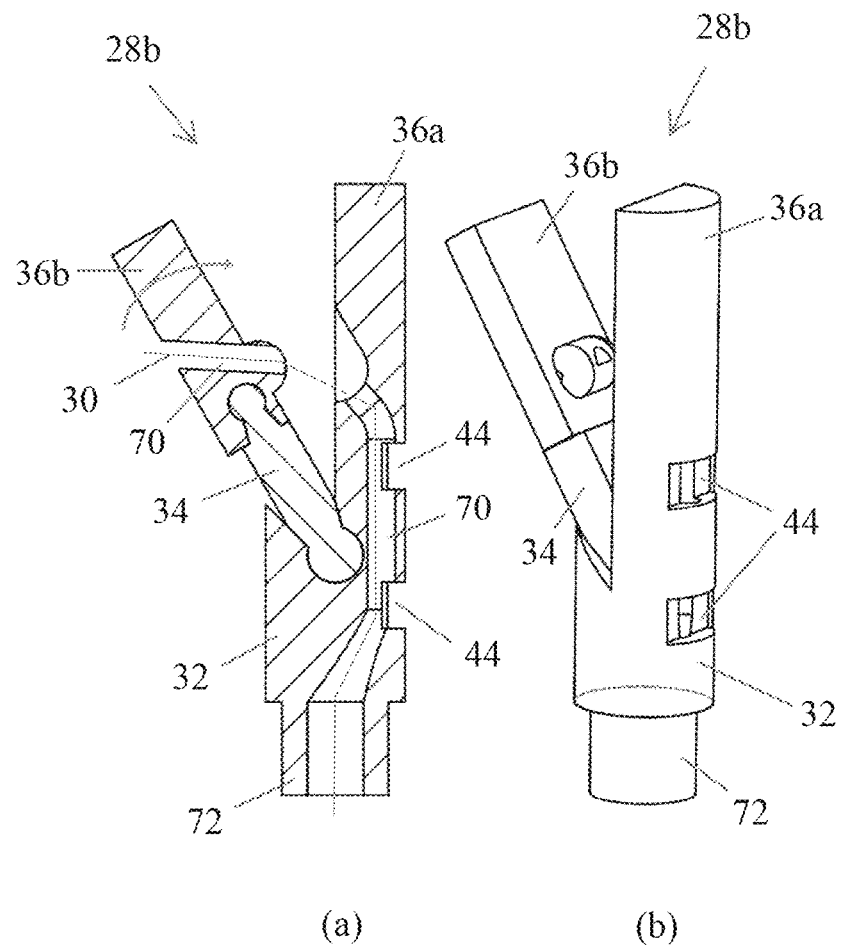
FIG. 6 includes images a and b, which are cross-sectional and perspective views, respectively, that schematically represent a nonlimiting working element configured as a grasper in accordance with a nonlimiting embodiment of this invention.

FIGS. 5 and 6 schematically represent nonlimiting embodiments of the nerve retractor 28a and grasper 28b, respectively, shown in FIG. 3. Images (a) of FIGS. 5 and 6 are cross sectional views of the retractor 28a and grasper 28b, respectively, and images (b) of FIGS. 5 and 6 are perspective views of the retractor 28a and grasper 28b, respectively. As described above in reference to FIG. 4, the retractor 28a if FIG. 5 includes a tip 36 coupled to a base 32 via a flexible joint 34. As represented, the retractor 28a includes passages 70 through which the guide wires 30 may be routed.

Figure 7A:
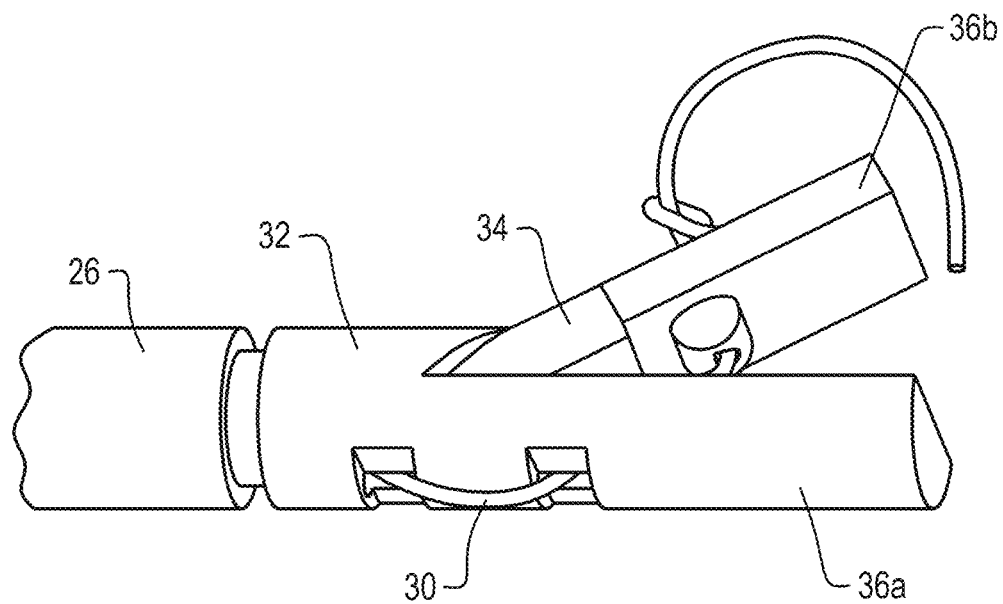
FIGS. 7a and 7b are images that show a grasper type tool in open and closed positions, respectively.
Figure 7B:
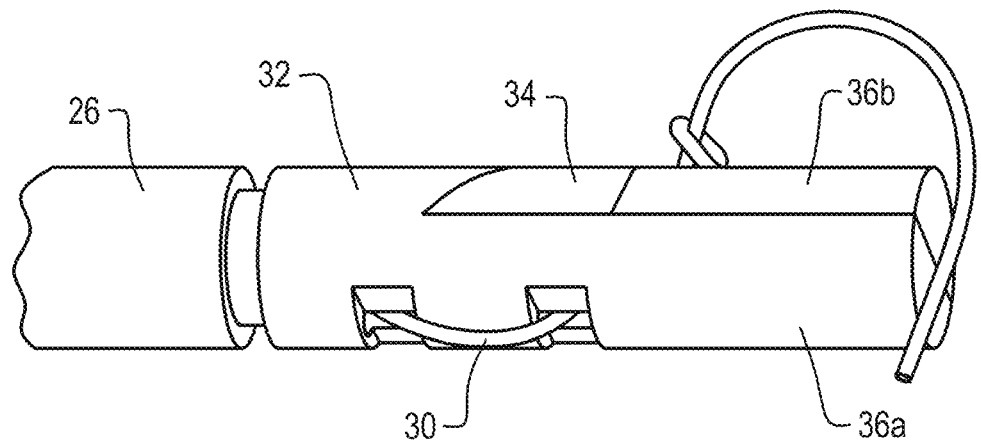

Referring to FIG. 6, the grasper 28b includes a first tip 36a directly coupled to a base 32 and fixed in a permanent position relative thereto, and a second tip 36b coupled to the base 32 by a flexible joint 34. The grasper 28b also includes passages 70 through which a guide wire 30 may be routed. Manipulation of the guide wire 30 provides for articulation of the second tip 36b relative to the base 32 and the first tip 36a. As such, the grasper 28b is capable of providing a gripping functionality by clasping an object between the first and second tips 36a and 36b. FIGS. 7a and 7b represents the grasper 28b in open and closed positions. During the procedure, the nerve retractor 28a of FIG. 5 may be used to articulate and retract a nerve such that the grasper 28b can access the cavity and remove herniated disk material 17 (FIG. 2c).

The various components of working elements 28 (including but not limited to the retractor 28a and grasper 28b) may be formed of a variety of suitable materials. Preferably, the base 32 and the tip 36 are formed of materials sufficiently rigid to perform their intended functions, and the joint 34 is sufficiently pliable or flexible such that the working element 28 may be articulated. Nonlimiting examples include various polymeric and elastic materials. A specific nonlimiting combination of materials includes a rubber-like polymeric material commercially available under the brand name Tango Black™ for the joint 34 and a rigid polymeric material commercially available under the brand name Vero White™ for the base 32 and tip 36, both materials produced by Stratasys Ltd. Alternatively, the two materials may be combined in various ratios individually specific to the base 32, joint 34, and tip 36 which provide a desired stiffness. Preferably, the working elements 28 are relatively small such that they can perform their respective tasks, rotate, and articulate with a confined working space or cavity, including relatively small confined working spaces having a volume of about three centimeters or less.

Although the various components of the working elements 28 could be separately produced and assembled, a preferred but nonlimiting aspect of the invention includes producing one or more of the working elements 28 with an additive manufacturing technique, such as but not limited to a three-dimensional printing technique that forms the various components as a single integral component by fusing particles together with, for example, a scanning electron, laser, or ion beam. Since the various components have different functions, it is likely that they may be formed of different materials, combinations of materials, or different ratios of their respective materials. Therefore, the working elements 28 are preferably produced with a multi-material three-dimensional printer. Forming the working elements 28 with such printing techniques may reduce assembly operations during production, reduce the cost of manufacturing, and/or provide individual users of the system 10 with the capability to design and produce custom working elements 28 to suit their individual needs. It is foreseeable that the working elements 28, especially those produced with an additive manufacturing technique, may have a sufficiently low cost such that they may be considered disposable. Therefore, it is within the scope of the invention that the working elements 28 may be removed from the shaft 26 and disposed after performing the procedure, rather than cleaning or sterilizing them for reuse.

Figure 9A:
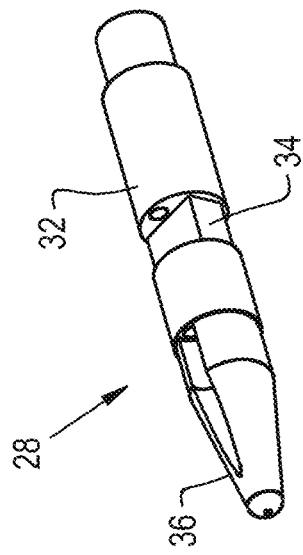
FIGS. 9A, 9B, 9C, and 9D depict steps performed in the production of a working element produced with a three-dimensional printing process.
Figure 9B:
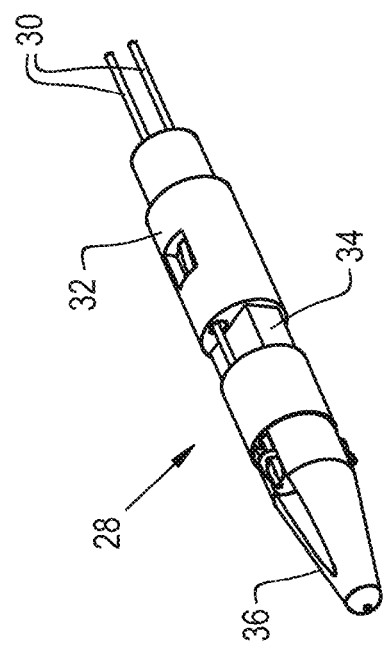
Figure 9C:
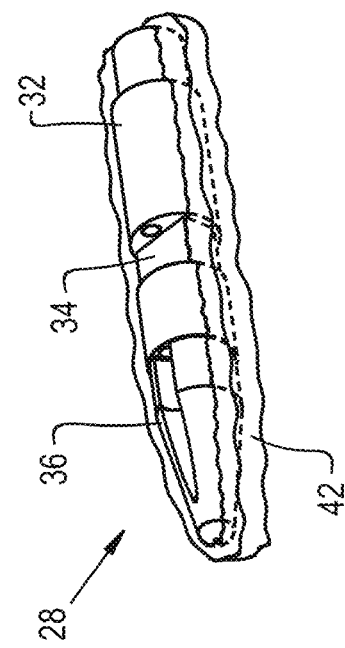
Figure 9D:
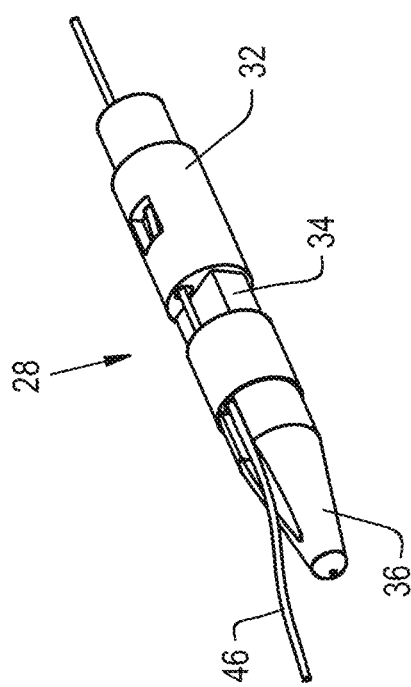

FIGS. 9A, 9B, 9C, and 9D contain images that sequentially represent steps in production of a working element 28 that was formed using an additive manufacturing technique, specifically a three-dimensional printing technique. The working element 28 was printed using a multi-material printer commercially available from Stratasys Ltd. under the brand name Objet350 Connex3™. After printing, the working element 28 was connected to support materials which were used to support and stabilize the working element 28 during the printing process. FIG. 9A shows the working element 28 encased in an external support material 42, FIG. 9B shows the working element 28 after the external support material 42 has been removed, and FIG. 9C shows a metal wire 46 being used to clear internal support material from passages configured to be used with the guide wires 30. The working element 28 includes ports 44 configured to facilitate removal of the internal support material by reducing the likelihood of clogging within the passages. FIG. 9D shows the final working element 28 with all support material removed and guide wires 30 routed therethrough.

As represented in FIGS. 1, 2 (image a), and 3, the system 10 may include a camera system that includes a tool 14 comprising a camera as the working element 28c. The camera may include a light source, or the system 10 may separately include a tool 14 with a light source as a working element 28. For example, the working element 28 may include a base 32, a flexible joint 34, and a tip 36 as described in reference to FIG. 4, wherein the tip 36 includes an integrated camera and light source. In such an embodiment, the joint 34 preferably allows the camera and light source to be capable of rotation relative to the cannula 12 and articulation relative to the shaft 26. It is also within the scope of the invention that multiple cameras and/or light sources may be used simultaneously with the system 10. Preferably, the camera and light source fit through the ports 24 in the adapter 22 and are capable of retracting into the body of the cannula 12. FIG. 1 and image (a) of FIG. 2 represent the monitor 20 functionally connected to the camera to provide images and/or video captured by the camera from the inside of the confined working space during the procedure. As nonlimiting examples, the camera and monitor 20 may have wireless communication capabilities or may be coupled with electrical wires routed through the shaft 26 of the tool 14.

The system 10 may include an irrigation system capable of cleaning a lens of the camera, for example, of accumulated fog or blood, or the confined working space in general. Such an irrigation system may include a sheath or tube (not shown) capable of fluidically transporting a cleaning solution and configured to be routed through the cannula 12 and protrude from one of the ports 24 at the distal end 13 of the cannula 12. Such an irrigation system may be capable of providing a cleaning solution to the lens of the camera and to the confined working space in general. The cleaning solution may be a fluid, for example, a gas, liquid, or gas or liquid mixture capable of providing the desired cleaning functionality. For surgical procedures performed within a living body, the cleaning solution may be, but is not limited to, a saline solution.

Figure 10:
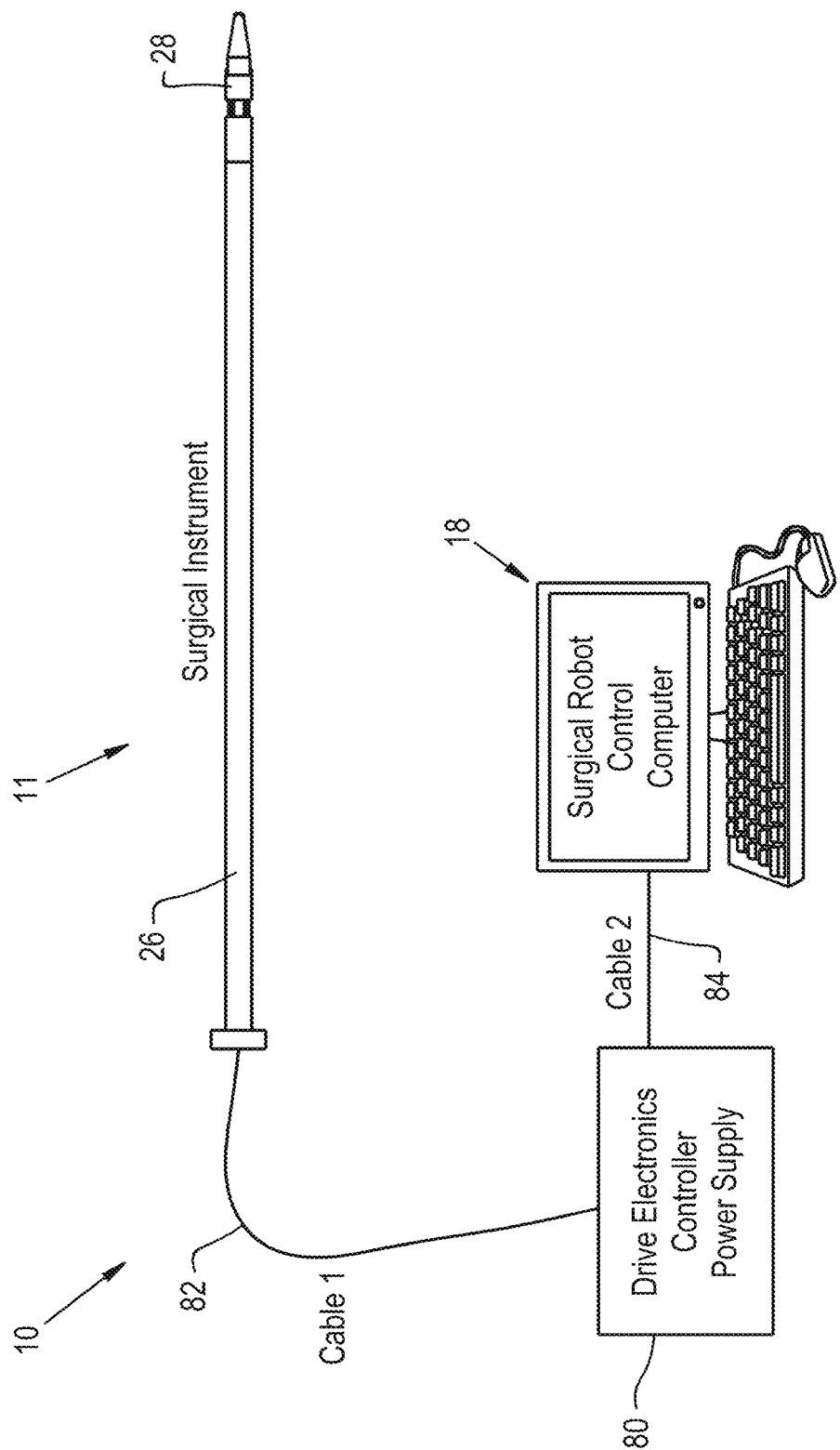
FIGS. 10 and 11 schematically represent alternative systems each comprising a surgical instrument equipped with multiple tools in accordance with a nonlimiting embodiment of this invention.
Figure 11:
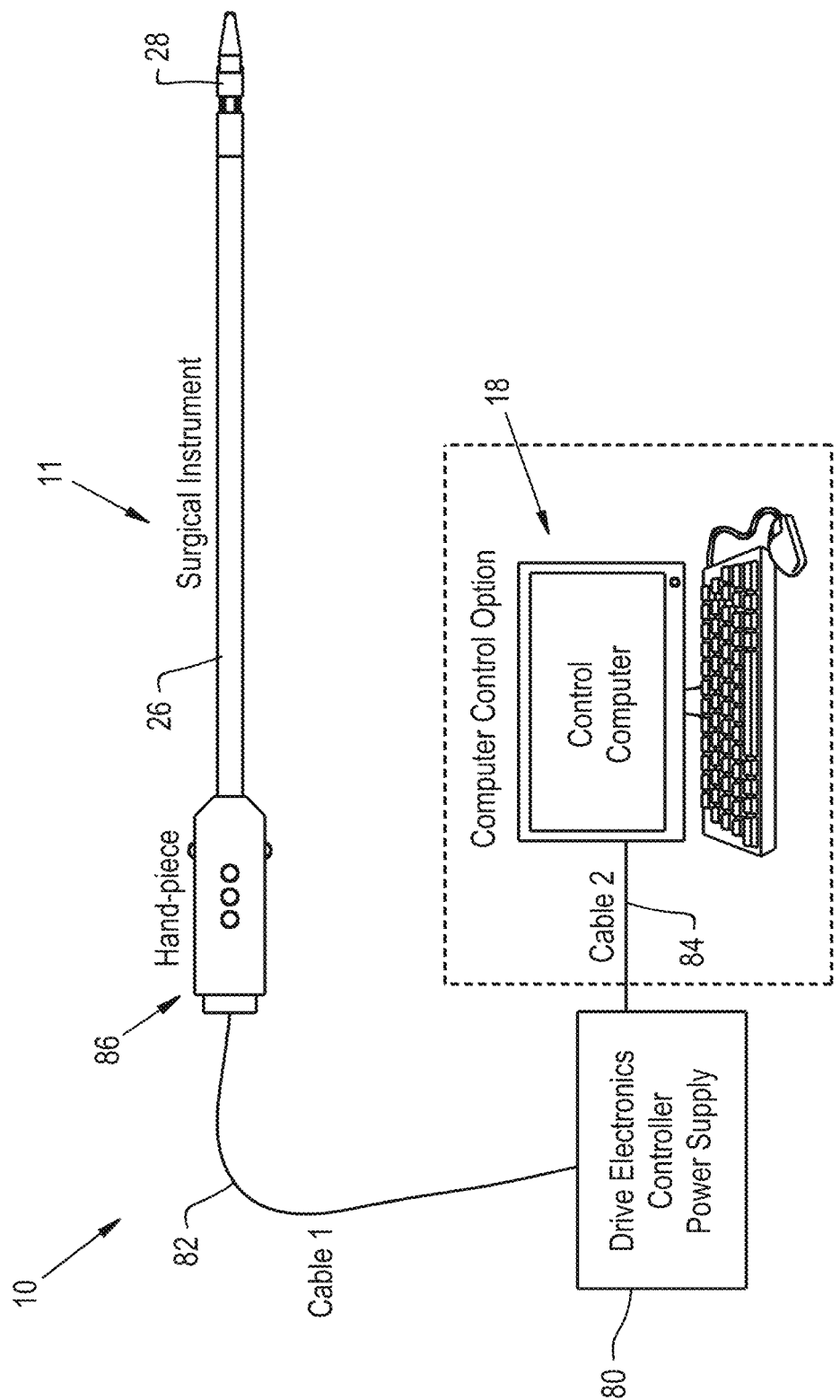

FIGS. 10 and 11 depict two additional embodiments for systems 10 suitable for performing minimally invasive surgery, and in particular the use of minimally invasive robotic spinal surgical instruments 11 that are compatible with, respectively, a surgical robot or an endoscopic system. In FIG. 10, the surgical instrument 11 is connected to a control system 18 in the form of a computer configured and operating as a surgical robot. The instrument 11 is connected to the control system 18 through a control unit 80 via a series of control cables 82 and 84. The control unit 80 comprises a power source, drive electronics, and controller (not shown) capable of translating the computer commands of the control system 18 into signals for actions to be carried out by the instrument 11. In this manner, robotic instrument control is capable of being integrated into the overall control architecture of the system 10.

In FIG. 11, the surgical instrument 11 is similarly connected to a control system 18 through a control unit 80 via a series of control cables 82 and 84. The system 10 primarily differs by the inclusion of an endoscopic hand-piece 86 mounted on the proximal end of the instrument 11, allowing for manual control of the instrument 11 and its working elements 28 instead of the robotic control of FIG. 10. The handpiece 86 includes interactive controls, as nonlimiting examples, buttons, switches, levers, etc., that allow the operator to control the instrument 11 in the workspace. As such, the cable 84 and control system 18 are not required, but may be included to provide an optional computer mode of operation for the system 10.

In the systems 10 of FIGS. 10 and 11, the instrument 11 and its working elements 28 can be actuated by smart material actuators integrated into the surgical instrument 11 and actuated from the control signals provided by the control system 18 or by the user through the hand-piece 86.

Figure 12:
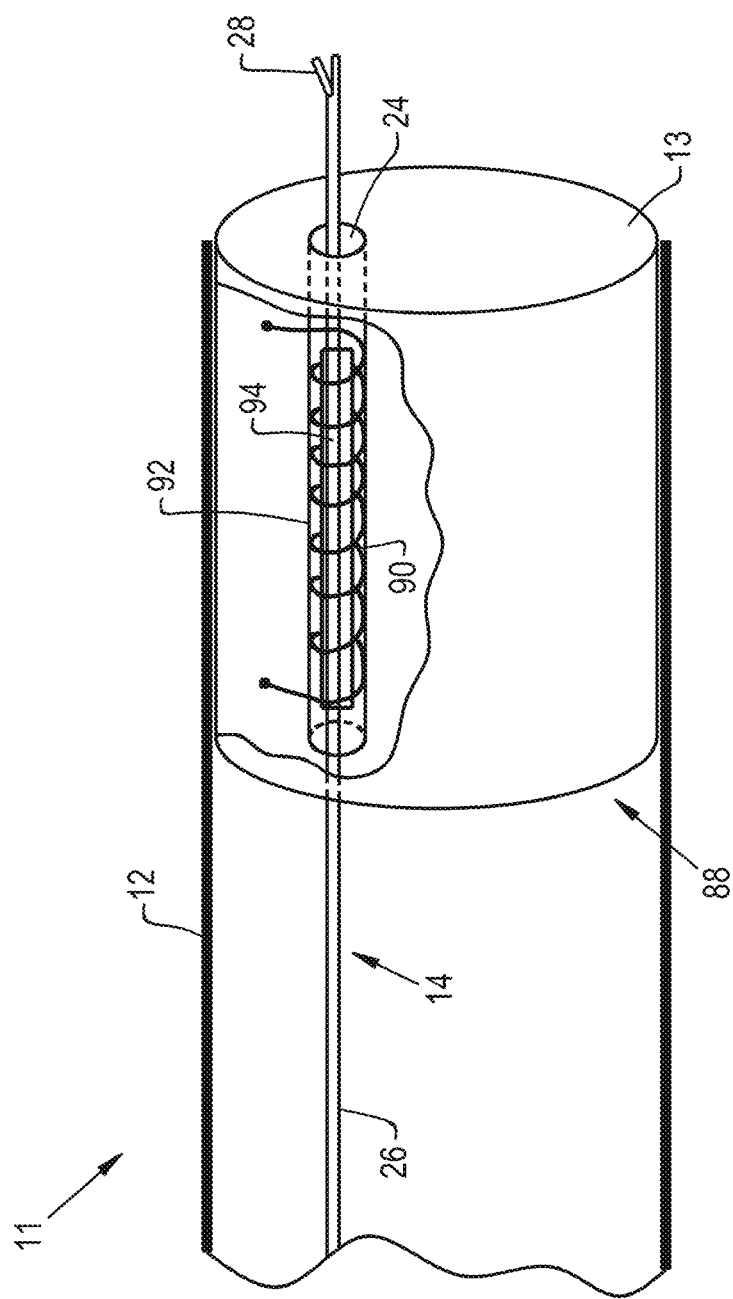
FIG. 12 schematically represents a surgical instrument comprising means for translating a tool thereof in accordance with a nonlimiting embodiment of this invention.
Figure 14:
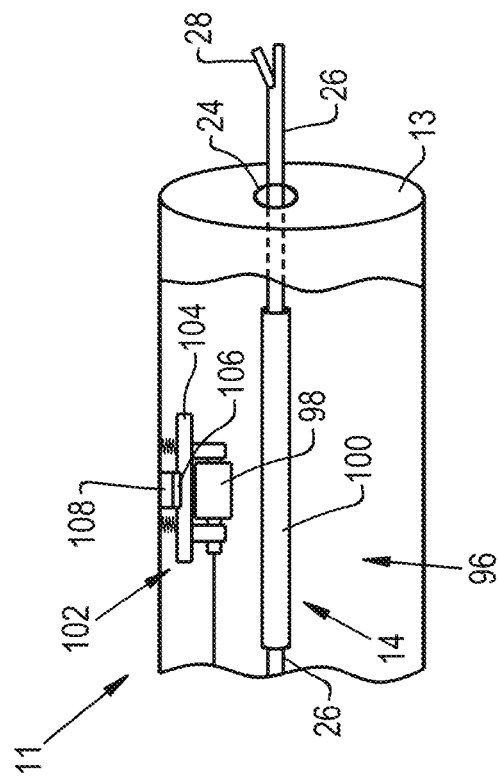
FIGS. 13 and 14 schematically represent a surgical instrument comprising means for rotating a tool thereof in accordance with a nonlimiting embodiment of this invention.
Figure 13:
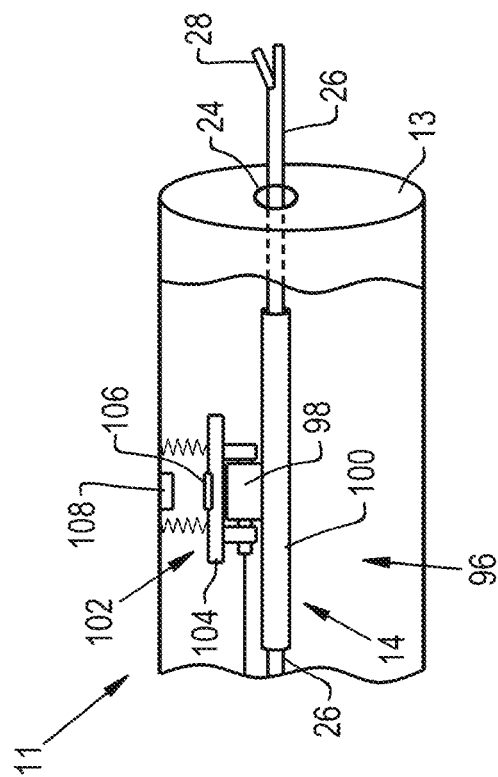

FIGS. 12, 13, and 14 schematically represent the distal end of the cannula 12 of the surgical instrument 11 and indicate how translational and rotational motions of individual tools 14 within the cannula 12 can be achieved with mechanisms internal of the cannula 12. The internal mechanisms are preferably computer controlled to independently translate and/or rotate a tool 14 and its working element 28, shown as protruding from a port 24 of the cannula 12. As such, control schemes previously described can be implemented at least in part with mechanisms integrated into the cannula 12 to allow for the linear translation of tools 14 in and out of a surgical workspace and/or allow for the axial rotation of tools 14 within a surgical workspace.

FIG. 12 represents a mechanism for achieving linear translational control of a tool 14 through the inclusion of a translation unit 88 internal of the cannula 12 and mounted at the distal end 13 of the cannula 12. The translation unit 88 may provide the port 24 through which the tool 14 protrudes from the cannula 12, and in so doing also serves as the adapter 22 described in reference to previous embodiments. The translation unit 88 further includes an actuation coil 90 surrounding a passage 92 within the unit 88 through which the shaft 26 of the tool 14 passes. The shaft 26 of the tool 14 can be formed of metallic material or, as represented in FIG. 12, wrapped with a metallic sheath 94 to enable the shaft 26 to serve as an armature. By causing current to flow through the actuation coil 90, the shaft 26 can function as an electromechanical solenoid to linearly translate the tool 14 and its working element 28. In the embodiment represented in FIG. 12, the shaft 26 will translate in one direction in response to current flow through the coil 26. A spring (not shown) can be integrated into the translation unit 88 to provide a restoring force to move the tool 14 in the opposite direction once current flow is discontinued. Alternatively, a duel solenoid system can be integrated into the translation unit 88 to provide bidirectional linear control of the translation of the tool 14.

FIGS. 13 and 14 represent a mechanism for achieving rotational control of a tool 14 through the inclusion of a rotation unit 96 internal and at the distal end 13 of the cannula 12. Similar to FIG. 12, the rotation unit 96 is depicted as providing the port 24 through which the tool 14 protrudes from the cannula 12. The rotation unit 96 is adapted to cause bidirectional rotational motion about the major axis of the tool 14 with a motorized rotary roller 98 that is in frictional contact with the tool shaft 26. A friction sheath 100 may be attached to the shaft 26 to promote frictional contact with the roller 98. To enable the translational unit 88 of FIG. 12 to be combined with the rotational control of FIGS. 13 and 14, FIGS. 13 and 14 represent an actuator 102 by which the roller 98 can be remotely engaged and disengaged from the shaft 26 of the tool 14. This actuator 102 is represented as comprising a spring-loaded mount 104 that is attached to the interior wall of the cannula 12, a magnet 106 carried by the mount 104, and an electromagnet 108 located on the wall of the cannula 12 opposite the magnet 106. Energizing and de-energizing the electromagnet 108 causes the roller 98 to engage or disengage the shaft 26 of the tool 14.

In view of the foregoing, the systems 10 described above provide functionality that may be used in surgical procedures and provide positive aspects of some of the most popular microdiscectomy procedures in aspects such as incision size and manipulation space utilization. Combined with the dexterity of the articulating working elements 28 and the feature of coordinated manipulation, the systems 10 may significantly aid surgeons in performing surgery and promote improved success rates. This may lead to reduced hospital stays, reduced chances of infection, and quicker recovery for their patients.

As a nonlimiting example, the systems 10 may be used, for example, by a surgeon to perform a surgical procedure within a cavity of a living body by inserting the distal end 13 of the body of the cannula 12 into the cavity of the living body, and therein perform various tasks of the surgical procedure with the working elements 28. Such tasks may require or be promoted by articulating the working element 28 relative to the shaft 26 within the cavity, and/or rotating the working element 28 relative to the cannula 12 within the cavity. It is foreseeable that a surgeon may produce one or more of the working elements 28 with an additive manufacturing technique that forms components of the working element 28 as a single integral component by fusing particles together, and then securing the working element 28 to a distal end of the shaft 26 of the tool 14 prior to performing the surgical procedure.

FIGS. 15 through 22 depict an additional embodiment of a surgical instrument 11 suitable for use when performing minimally invasive surgery, such as minimally invasive robotic spinal surgery. In these figures, consistent reference numbers are used to identify the same or functionally related/equivalent elements described for the embodiments of FIGS. 1 through 14. In view of similarities between the embodiments, the following discussion of FIGS. 15 through 22 will focus primarily on aspects of the embodiment depicted therein that differ from the previous embodiments in some notable or significant manner. Other aspects of the embodiment of FIGS. 15 through 22 not discussed in any detail can be, in terms of structure, function, materials, etc., essentially as was described for the previous embodiments.

Figure 15:
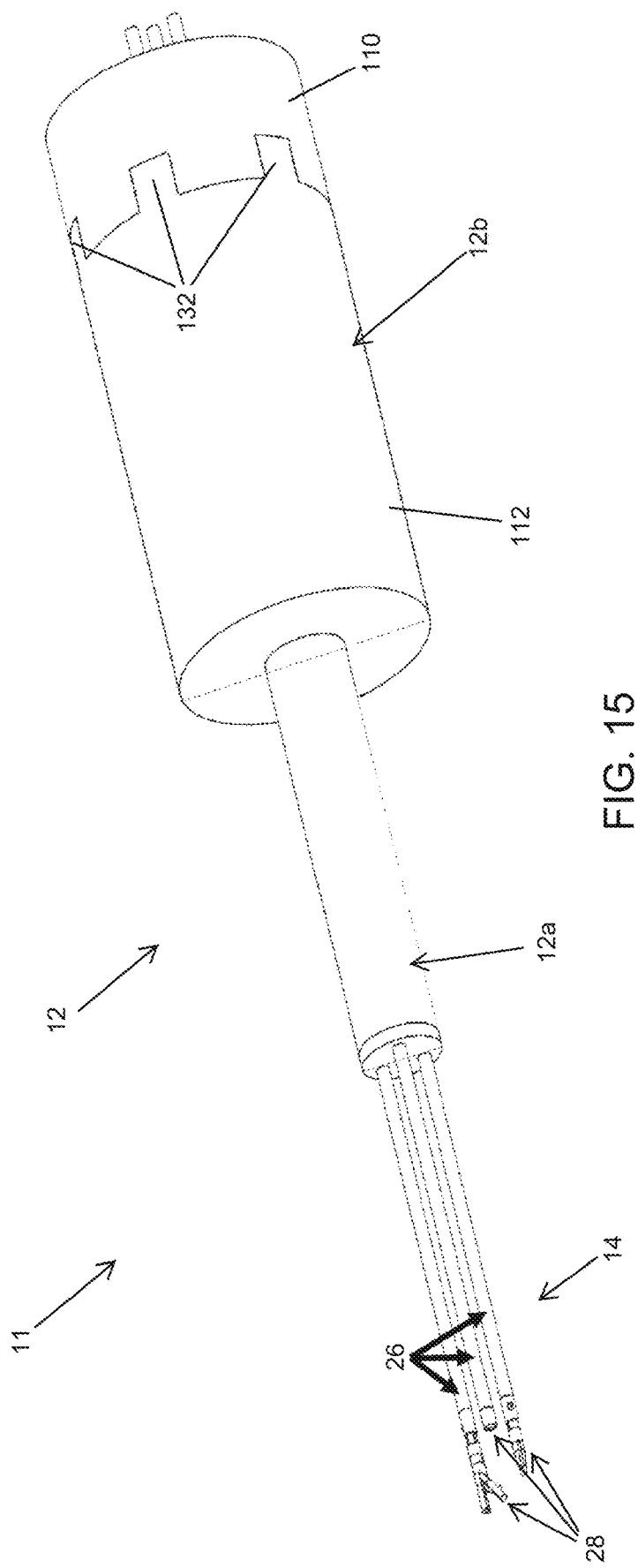
FIG. 15 schematically represents a surgical instrument equipped with multiple tools for performing tasks in an enclosed space and means for individually and independently translating and rotating the tools in accordance with another nonlimiting embodiment of the invention, and FIGS. 16 through 22 schematically represent various components and subassemblies of the instrument of FIG. 15.

FIG. 15 schematically represents the surgical instrument 11 as comprising multiple tools 14 extending from a cannula 12, and FIGS. 16 through 22 schematically represent various components and subassemblies of the instrument 11 of FIG. 15 that include means for individually and independently translating and rotating the tools 14. FIG. 15 represents the cannula 12 as having a distal portion 12a adapted to be inserted into a patient during a surgical procedure, and a proximal portion 12b adapted to reside outside of the body of the patient during the procedure. The distal portion 12a has a smaller diameter than the proximal portion 12b, as nonlimiting examples, a diameter of approximately 19 mm to allow for a minimally invasive incision (e.g., less than 25 mm), as compared to a diameter of approximately 60 mm for the proximal portion 12b. The tools 14 are inserted from the rear of the proximal portion 12b of the cannula 12 and extend through ports at a distal end of the distal portion 12a to place the working elements 28 of the tools 14 in a surgical workspace where a surgeon can teleoperate them to perform a surgical procedure.

Figure 16:
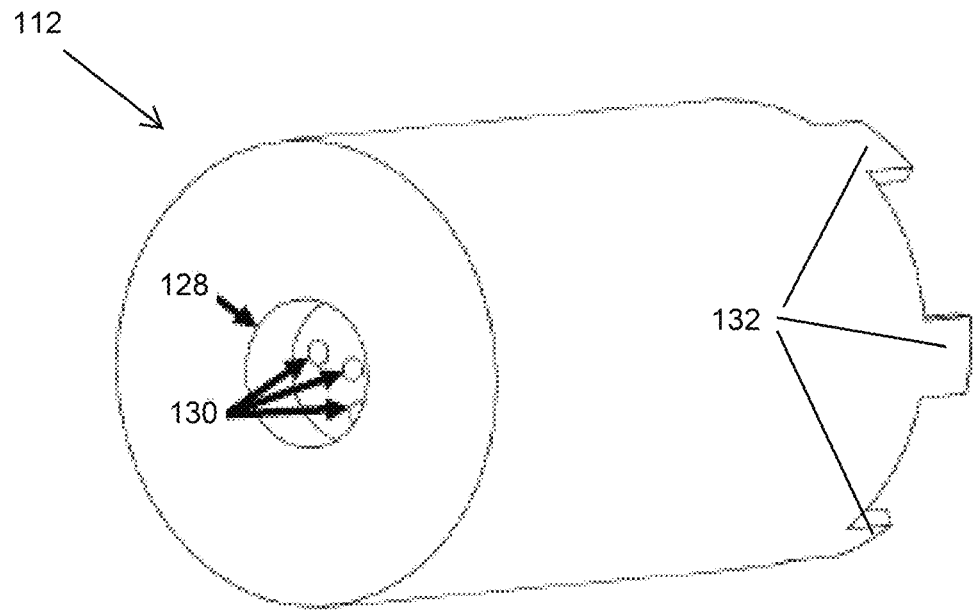
Figure 17:
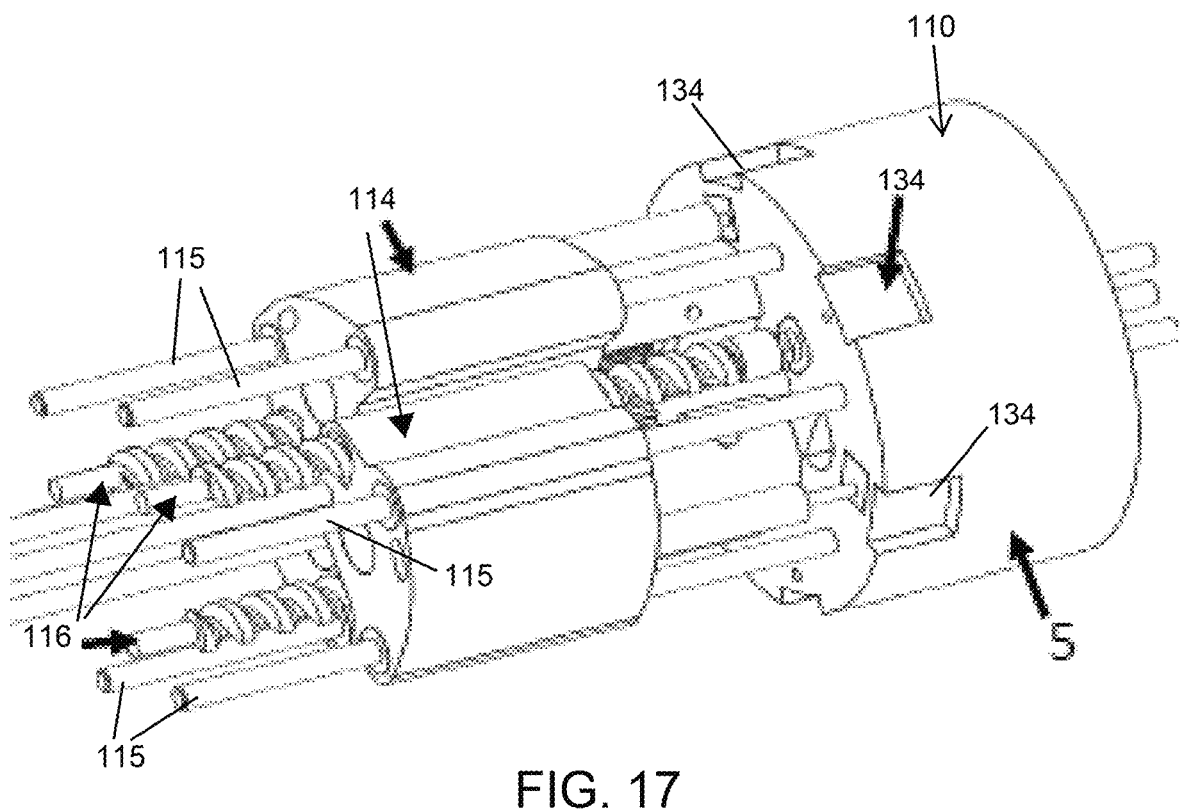

As represented in FIGS. 15 through 17, the proximal portion 12b of the cannula 12 includes a base 110 (FIG. 17) and an outer housing 112 (FIG. 16) that encloses the means for individually and independently translating and rotating the tools 14. In the nonlimiting embodiment of FIGS. 15 through 22, the translating and rotating means comprise the base 110 and multiple carriage units 114, which in combination incorporate translation and rotation mechanisms for individually and independently translating and rotating each of the tools 14. In particular, each carriage unit 114 provides the capability to individually and independently translate and rotate the tool 14 associated therewith, and this capability is independent of the ability of other carriage units 114 to translate and rotate their respective tools 14. As will be described below in reference to FIGS. 21 and 22, the shafts 26 of the individual tools 14 are inserted and locked into their corresponding carriage units 114, each of which is individually and slidably mounted on multiple journal rods 115 that are mounted to and extend from the base 110 to permit translation of the carriage units 114 in axial directions of the cannula 12. In the nonlimiting embodiment of FIGS. 15 through 22, each translation mechanism includes a worm gear 116 that is threadably engaged with a rack 120 carried by the corresponding carriage unit 114 and is driven by a motor 118 located on the base 110 to controllably cause the carriage unit 114 to translate in the axial directions of the cannula 12. Also in the nonlimiting embodiment of FIGS. 15 through 22, each rotation mechanism includes a drive gear 122, a drive motor 124, and a driven gear 126 that are all mounted on a corresponding carriage unit 114 and cooperate to controllably cause the shaft 26 of their corresponding tool 14 to rotate about the axis of the shaft 26 and relative to its carriage unit 114.

Figure 18:
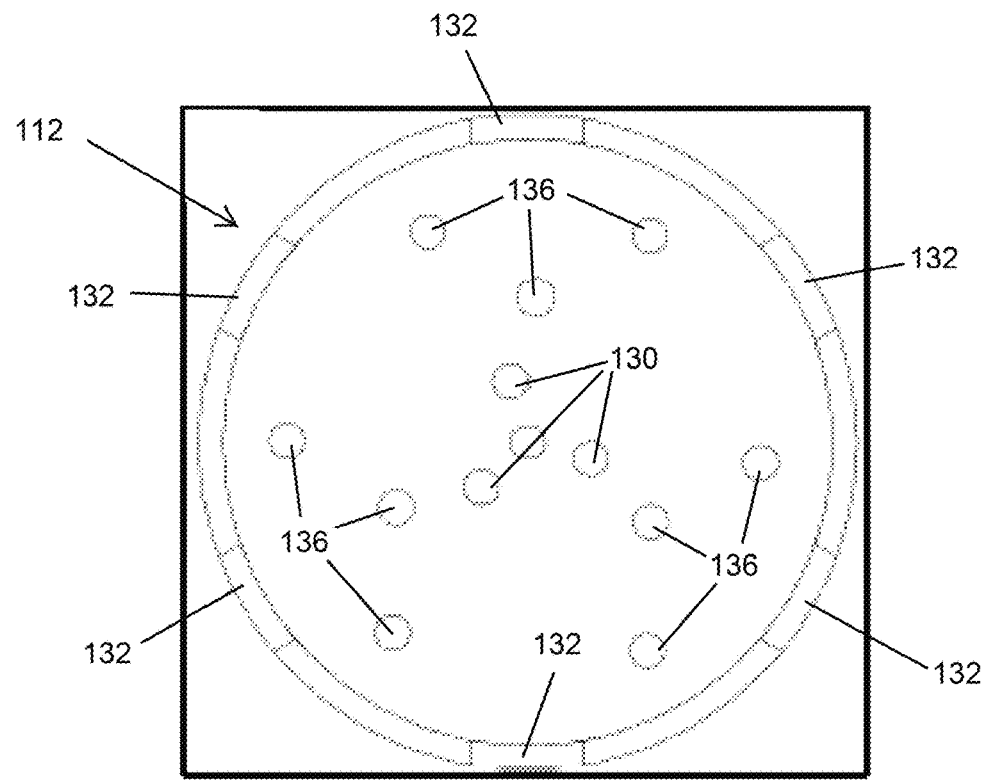
Figure 22:
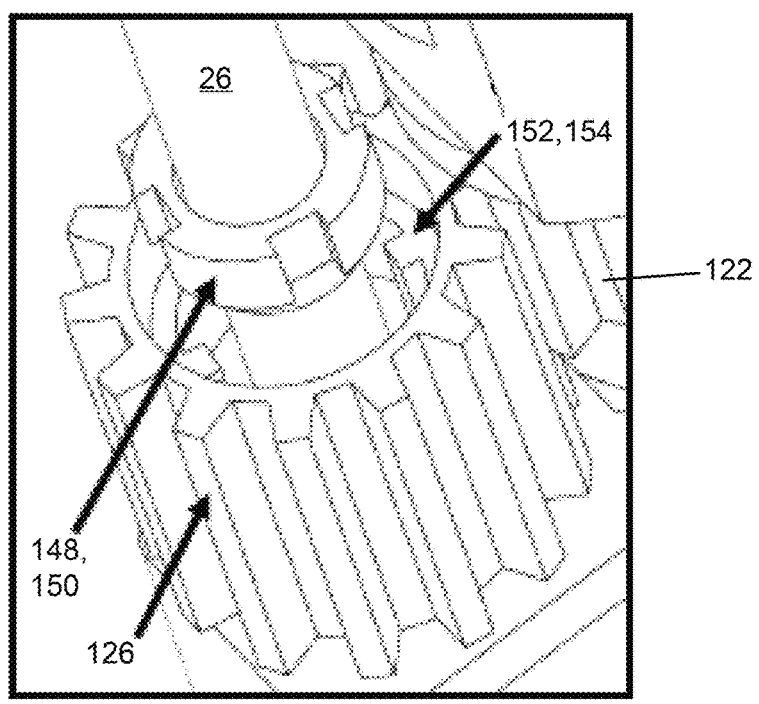

The housing 112 of the proximal portion 12b of the cannula 12 is shown in FIG. 16 as having a circular recess 128 to couple the distal portion 12a of the cannular 12 to the proximal portion 12b, and the shafts 26 of the tools 14 pass through holes 130 within the recess 128. As represented in FIG. 17, the translation and rotation mechanisms, including the carriage units 114, are mounted to and supported by the base 110 of the proximal portion 12b of the cannula 12. With the base 110, the housing 112 of the proximal portion 12b fully encloses the translation and rotation mechanisms and is retained on the base 110 with latches 132 that engage complementary slots 134 on the base 110. In FIG. 17, three tools 14 are independently assembled and individually and independently controlled with three carriage units 114, though it is foreseeable that the instrument 11 could comprise fewer or greater numbers of tools 14 and carriage units 114. FIG. 18 depicts the housing 112 as having blind holes 136 internally located at its distal end to constrain distal ends of the journal rods 115 and worm gears 116.

Figure 19:
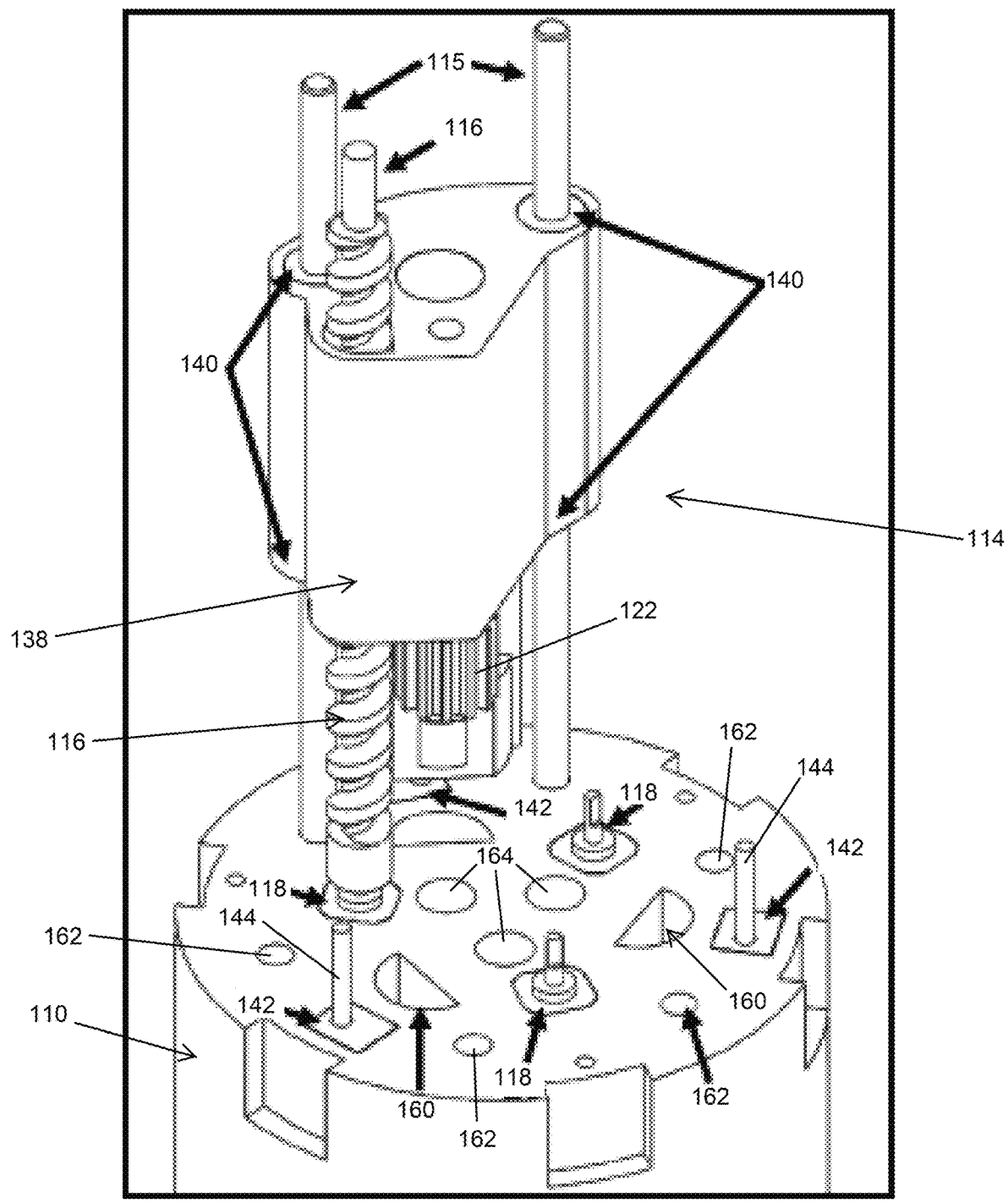
Figure 20:
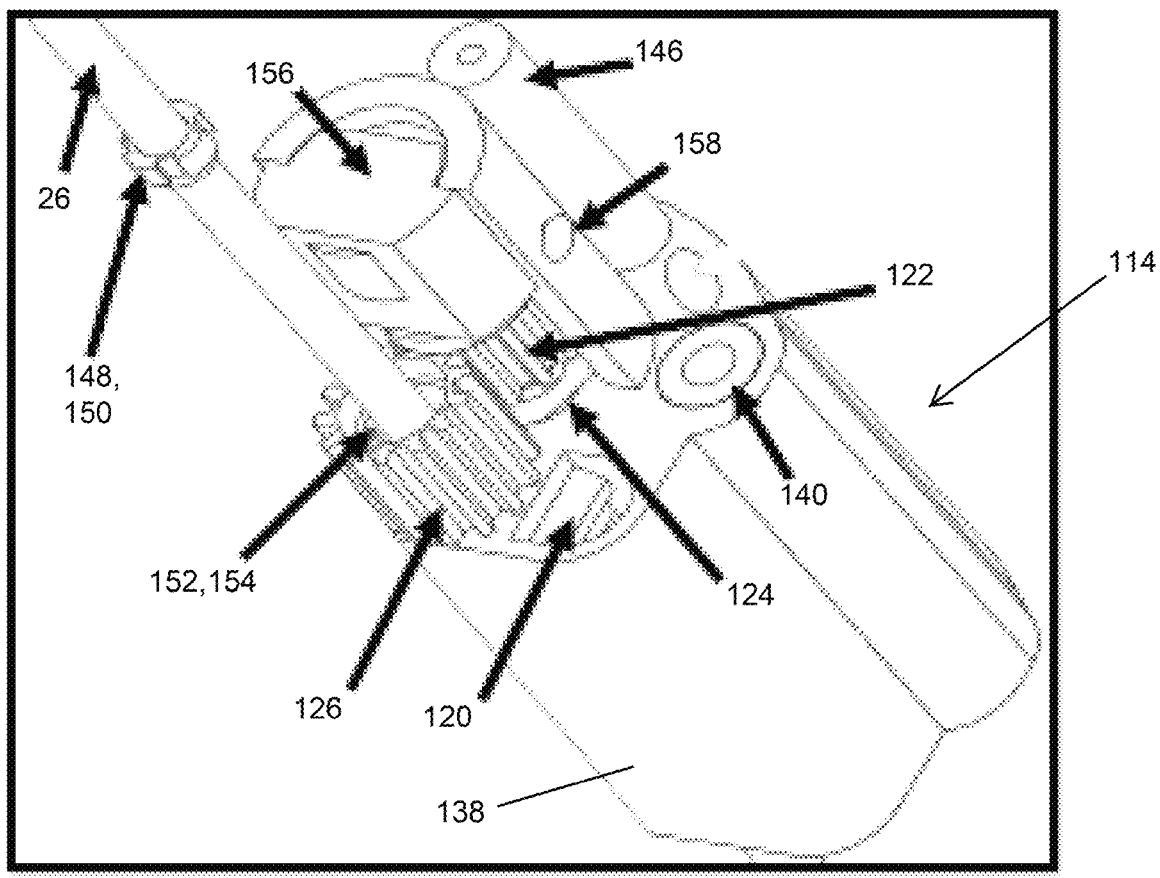
Figure 21:
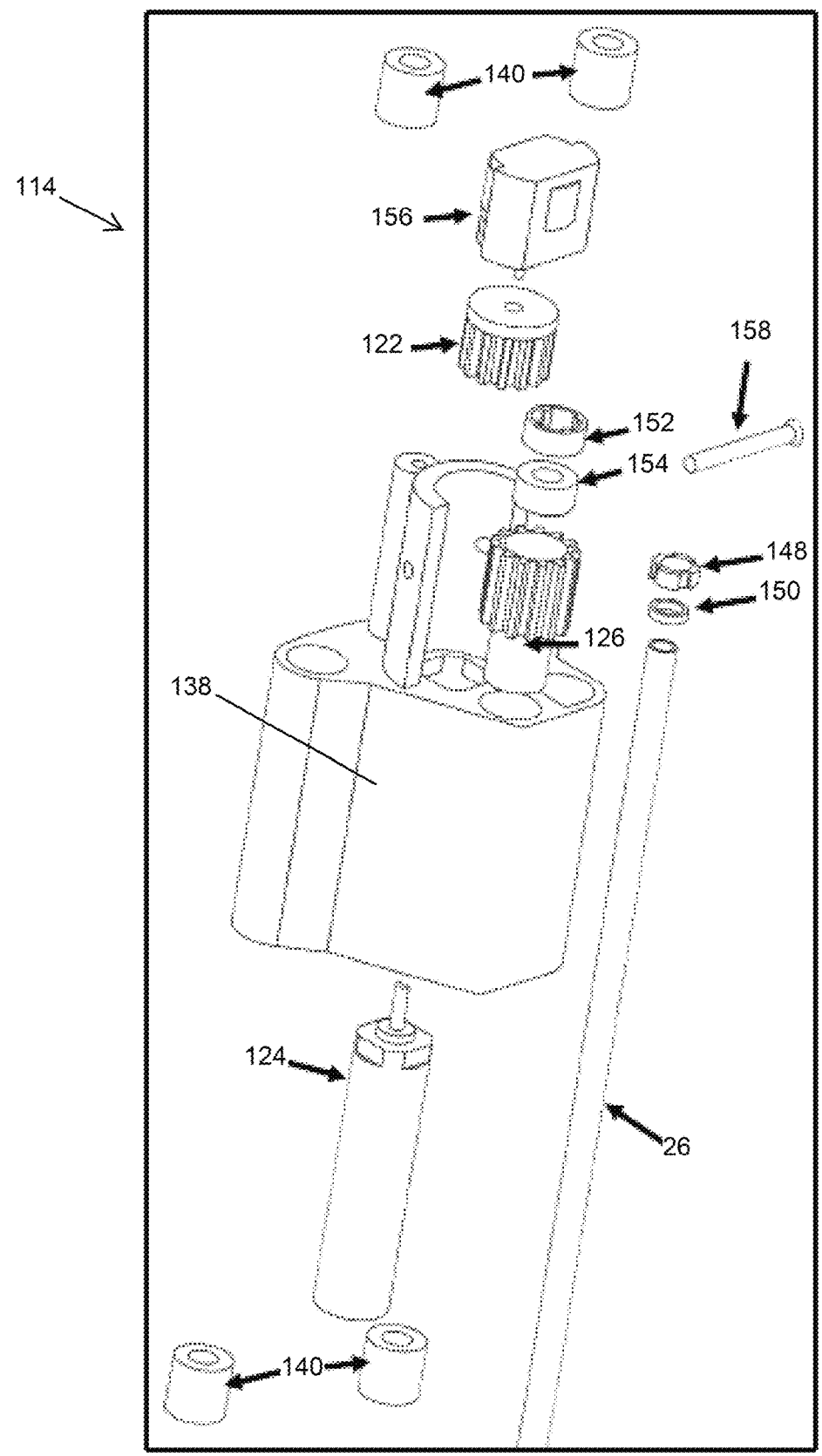

FIG. 19 shows an individual carriage unit 114 mounted to the base 110, FIG. 20 shows a proximal view of the carriage unit 114 of FIG. 19 after its removal from the base 110, and FIG. 21 is an exploded view of the carriage unit 114 of FIGS. 19 and 20. As previously described, the translation mechanism associated with each carriage unit 114 includes the worm gear 116 (FIG. 19) and the rack 120 (FIG. 20) with which the worm gear 116 is engaged, and the motor 118 located on the base 110 for rotating the worm gear 116 to controllably cause the carriage unit 114 to translate in the axial directions of the cannula 12. As seen in FIG. 20, the rack 120 is formed within a passage defined within a body 138 of the carriage unit 114 to which other components of the carriage unit 114 are mounted. As the motor 118 rotates, the worm gear 116 and rack 120 cooperate to cause the carriage unit 114 to translate along the journal rods 115 that support the carriage unit 114 on the base 110. Translation of the carriage unit 114 is facilitated with sleeve bearings 140 fixed in the body 138 of the carriage unit 114. The ratio between the rotation of the worm gear 116 and translation of the carriage unit 114 (and therefore the translation of the tools 14) may be, as a nonlimiting example, about 1:5 revolutions/mm. FIGS. 19 and 20 further depict linear motion potentiometers 142 embedded in the base 110 for sensing the distance that the carriage unit 114 and its tool 14 translate. A shaft 144 (FIG. 19) of each potentiometer 142 protrudes from the base 110 to be slidably received in a sleeve 146 (FIG. 20) mounted to the body 138 of the carriage unit 114.

As previously described, the rotation mechanism associated with each carriage unit 114 includes the drive gear 122 (FIGS. 19 through 22) driven by the motor 124 (FIGS. 20 and 21) and meshed with the driven gear 126 (FIGS. 20 through 22) that is attached to the tool shaft 26 (FIGS. 20 and 22), all of which are mounted on the corresponding carriage unit 114 for controllably causing the shaft 26 of their corresponding tool 14 to rotate about the axis of the shaft 26 and relative to the corresponding carriage unit 114. The gear ratio between the gears 122 and 126 may be, as a nonlimiting example, about 1:1. As more readily seen in FIGS. 21 and 22, a locking collar 148 assembled with a ring magnet 150 is attached to the tool shaft 26, and a locking collar 152 assembled with a ring magnet 154 is mounted to the driven gear 126 of the rotation mechanism. The tool shaft 26 is assembled with the carriage unit 114 so that it passes through the center of the gear 126, slots on the collar 148 are engaged by teeth on the collar 152, and their respective magnets 150 and 154 are attracted and attach to each other to releasably maintain the collars 148 and 152 in their engaged positions so that rotation of the driven gear 126 induced by the drive gear 122 and motor 124 is transferred to the tool shaft 26, while also permitting the tool shaft 26 to be removed from the carriage unit 114 by simply overcoming the magnetic forces of the magnets 150 and 154. A rotary potentiometer 156 is mounted to the carriage unit 114 to measure the rotation of the shaft 26. In the nonlimiting embodiment shown, a shaft of the potentiometer 156 is coupled with the drive gear 122 so that rotation of the tool shaft 26 is read through the rotation of the drive and driven gears 122 and 126. The potentiometer 156 is represented as being secured to the carriage unit 114 with a bolt 158.

From the above, it is apparent that the carriage unit 114 represented in FIGS. 19 through 20 enables the tool 14 associated therewith to be selectively translated and/or rotated, and this capability is independent of the ability of other carriage units 114 (e.g., FIG. 17) to selectively translate and/or rotate their respective tools 14, as may be appropriate or necessary during a surgical procedure.

FIG. 19 further represents through-holes 160 in the body 138 of the carriage unit 114 through which wiring (not shown) can be routed to the potentiometers 142 and 156 and motors 118 and 124, holes 162 for mounting drive rods 115, and holes 164 through which the tool shafts 26 pass through the central region of the bass 110. The motors 118 and 124 can be controlled by a control system (e.g., 18 of FIGS. 1 and 10) to control the translation and rotation mechanisms to cause the tools 14 of any or all of the carriage units 114 to individually and independently translate and rotate relative to the cannula 12, with positional feedback being provided by the potentiometers 142 and 156.

While the invention has been described in terms of specific embodiments, it is apparent that other forms could be adopted by one skilled in the art. For example, the physical configuration of the systems 10 and their various components could differ from that shown, and materials and processes/methods other than those noted could be used. In addition, the invention encompasses additional or alternative embodiments in which one or more features or aspects of a particular embodiment could be eliminated or two or more features or aspects of different disclosed embodiments could be combined. Accordingly, it should be understood that the invention is not necessarily limited to any embodiment described herein or illustrated in the drawings. Therefore, the scope of the invention is to be limited only by the following claims.

The invention claimed is:

1. A system for performing a surgical procedure within a cavity of a living body, the system comprising:
a cannula having a proximal portion, a distal portion sized and configured to be inserted into the cavity, and multiple ports located at a distal end of the distal portion;
at least a first carriage unit and a second carriage unit that are each slidably mounted within the proximal portion of the cannula for translation in axial directions of the cannula;
at least a first tool having a shaft coupled to the first carriage unit and protruding through at least a first port of the multiple ports of the distal portion of the cannula, the first tool comprising a first working element mounted on a portion of the shaft that protrudes from the cannula, the first working element being configured to perform tasks within the cavity;
at least a second tool having a shaft coupled to the second carriage unit and protruding through at least a second port of the multiple ports of the distal portion of the cannula, the second tool comprising a second working element mounted on a portion of the shaft of the second tool that protrudes from the cannula, the second working element being configured to perform at least one additional task within the cavity;
a first translation mechanism for translating the first carriage unit and the first tool thereof in the axial directions of the cannula;
a first rotation mechanism for rotating the first tool about an axis of the shaft of the first tool and relative to the first carriage unit;
a second translation mechanism for translating the second carriage unit and the second tool thereof in the axial directions of the cannula independently of the first tool of the first carriage unit; and
a second rotation mechanism for rotating the second tool about an axis of the shaft of the second tool and relative to the second carriage unit independently of the first tool of the first carriage unit.

2. The system of claim 1, wherein the first translation mechanism comprises a rack associated with the first carriage unit and meshed with a motor-driven worm gear.

3. The system of claim 2, wherein the worm gear is driven by a gear mounted to a base of the proximal portion of the cannula and the worm gear is carried by the first carriage unit.

4. The system of claim 2, further comprising means mounted to the first carriage unit for sensing a translation distance of the first carriage unit.

5. The system of claim 1, wherein the first rotation mechanism comprises a motor-driven drive gear meshed with a driven gear that are carried by the first carriage unit.

6. The system of claim 5, wherein the shaft of the first tool is magnetically coupled to the driven gear.

7. The system of claim 5, further comprising means mounted to the first carriage unit for sensing rotation of the shaft of the first tool.

8. The system of claim 1, further comprising:
a control system operable to individually and independently control the first translation mechanism and the first rotation mechanism of the first carriage unit and the second translation mechanism and the second rotation mechanism of the second carriage unit.

9. The system of claim 1, wherein the proximal portion of the cannula comprises a base and a housing that encloses the first carriage unit, the first translation mechanism, and the first rotation mechanism.

10. The system of claim 9, further comprising journal shafts protruding from the base and on which the first carriage unit is slidably mounted for translation relative to the base.

11. The system of claim 1, wherein the first working element comprises a base, a flexible joint directly coupled to the base, and at least a first portion coupled to the base by the flexible joint and capable of articulation relative to the base and the shaft and rotation relative to the cannula.

12. The system of claim 11, wherein the first working element is produced with an additive manufacturing technique so that the base, the flexible joint, and the first portion of the first working element are a single integral component as a result of the base, the flexible joint, and the first portion being formed by particles fused together.

13. The system of claim 12, wherein the flexible joint is formed of a flexible material such that the first portion is able to articulate relative to the base, and the base and the first portion are formed of materials that are different than the flexible material of the flexible joint so that the base and the first portion are more rigid than the flexible material of the joint.

14. The system of claim 13, wherein the flexible material of the flexible joint has a first end embedded in the material of the base and an oppositely disposed second end embedded in the material of the first portion.

15. The system of claim 14, further comprising a guide wire associated with the first tool, the guide wire being routed through the shaft to the first portion of the first working element to articulate the first portion.

16. The system of claim 15, further comprising an actuator unit functionally coupled to the guide wire and operable to selectively apply or release tension on the guide wire to articulate a tip of the first working element of the first tool.

17. The system of claim 1, further comprising a control system operable to individually and independently control the first translation mechanism and the first rotation mechanism of the first carriage unit.

18. The system of claim 1, further comprising a camera system and an irrigation system.

19. The system of claim 1, wherein the first working element of the first tool is chosen from the group consisting of a nerve retractor, a surgical manipulator, a camera, a suction tip of an irrigation system, and a drill.

20. The system of claim 1, wherein the surgical procedure is a microdiscectomy and the cavity has a volume of three cubic centimeters or less.

* * * * *